United States Patent [19]
Erichsen et al.

[11] Patent Number: 5,004,683
[45] Date of Patent: Apr. 2, 1991

[54] MEANS FOR DETECTING AND ANALYZING NEUROANATOMY

[75] Inventors: Jonathan T. Erichsen, Stony Brook; Craig Evinger, Huntington; Harvey J. Karten, Setauket, all of N.Y.

[73] Assignee: The Research Foundation of State University of New York, Albany, N.Y.

[21] Appl. No.: 254,447

[22] Filed: Oct. 6, 1988

Related U.S. Application Data

[63] Continuation of Ser. No. 892,191, Jul. 31, 1986, abandoned.

[51] Int. Cl.$^5$ .................. G01N 33/53; G01N 33/567; G01N 33/577; A61K 49/00
[52] U.S. Cl. ........................................ 435/7.21; 424/9; 436/501; 436/503; 436/543; 436/548; 436/63; 436/811; 435/960
[58] Field of Search ..................... 435/7, 172.2, 240.27; 436/503, 548, 811, 501, 543, 63; 530/387; 424/9

[56] References Cited

U.S. PATENT DOCUMENTS 4,444,744  4/1984  Goldenberg .......................... 424/1.1

OTHER PUBLICATIONS

Evinger, C. and Erichsen, J. T., "Transsynaptic Retrograde Transport of Fragment C of Tetanus Toxin Demonstrated by Immunohistochemical Localization," Brain Research, 380, 383-388 (1986).
Manning, K. A., Erichsen, J. T. and Evinger, C., "Retrograde Transneuronal Transport Properties of Fragment C of Tetanus Toxin," Neuroscience 34, 251-263 (1990).
Bizzini, B., Grob, P. & Akert, K. (1981), Papain-Derived Fragment IIc of Tetanus Toxin: Its Biding to Isolated Synaptic Membranes and Retrograde Axonal Transport, Brain Res., 210: 291-299.
Black, M. M. & Lee, V. M.-Y. (1988), Phosphorylation of Neurofilament Proteins in Intact Neurons: Demonstration of Phosphorylation in Cell Bodies and Axons, J. Neurosci., 8: 3296-3303.
Borges, L. F. & Sidman, R. L. (1982), Axonal Transport of Lectins in the Peripheral Nervous System, J. Neurosci., 2: 647-653.
Buttner-Ennever, J. A., Grob, P., Akert, K. & Bizzini, B. (1981a), Transsynaptic Retrograde Labeling in the Oculomotor System of the Monkey with [$^{125}$I] Tetanus Toxin BII$_b$ Fragment, Neurosci. Lett., 26: 233-238.
Buttner-Ennever, J. A., Grob, P. & Akert, K. (1981b), A Transsynaptic Autoradiographic Study of the Pathways Controlling the Extraocular Eye Muscles, Using [$^{125}$I]B-II$_b$ Tetanus Toxin Fragment, Ann. N.Y. Acad. Sci., 374: 157-170.
Harrison, P. J., Hultborn, H., Jankowska, E., Katz, R., Storai, B. & Zytnicki, D. (1984), Labeling of Interneurones by Retrograde Transsynaptic Transport of Horseradish Peroxidase from Motoneurones in Rats and Cats, Neurosci. Lett., 45: 15-19.
Porter, J. D., Guthrie, B. L. & Sparks, D. L. (1985), Selective Retrograde Transneuronal Transport of Wheat Germ Agglutinin-Conjugated Horseradish Peroxidase in the Oculomotor System, Exp. Brain Res., 57: 411-416.
Schmidt, M. L. & Trojanowski, J. Q. (1985), Immunoblot Analysis of Horseradish Peroxidase Conjugates of Wheat Germ Agglutinin Before and After Retrograde Transport in the Rat Peripheral Nervous System, J. Neurosci., 5: 2779-2785.
Schwab, M. E. & Thoenen, H. (1976), Electron Microscopic Evidence for a Transsynaptic Migration of Tetanus Toxin on Spinal Cord Motoneurons: An Autoradiographic and Morphometric Study, Brain Res., 105: 213-227.
Schwab, M. E., Agid, Y., Glowinski, J. & Thoenen, H. (1977), Retrograde Axonal Transport of [$^{125}$I] Tetanus Toxin as a Tool for Tracing Fiber Connections in the Central Nervous System: Connections of the Rostral Part of the Rat Neostriatum, Brain Res., 126: 211-224.
Schwab, M. E., Suda, K. & Thoenen, J. (1979), Selective Retrograde Transsynaptic Transfer of a Protein Tetanus Toxin, Subsequent to Its Retrograde Axonal Transport, J. Cell Biol., 82: 798-810.
Schwab et al, Brain Research, vol. 122, 1977, pp. 459-474.
Simpson, The J. of Pharm. and Exper. Therapeutics, vol. 234, 1985, pp. 100-105.
Simpson et al, The J. of Pharm. and Exper. Therapeutics, vol. 232, 1985, pp. 223-227.
Kenimer et al, Infection and Immunity, vol. 42, Dec. 1983, pp. 942-948.
Sheppard et al, Infection and Immunity, vol. 43, Feb. 1984, pp. 710-714.
Polakis et al, Archives of Biochemistry and Biophysics, vol. 234, Nov. 1984, pp. 341-352.
Critchley et al, The J. of Cell Biology, vol. 100, May 1985, pp. 1499-1507.
Critchley et al, J. of Neurochemistry, vol. 47, 1986, pp. 213-222.
Willinger, Neuroimmunology, "Probing Neuronal Differentiation with Cholera Toxin", edited by P. Behan et al, Raven Press, New York, 1984, pp. 11-22.

Primary Examiner—Esther L. Kepplinger
Assistant Examiner—Florina B. Hoffer
Attorney, Agent, or Firm—Hoffmann & Baron

[57] ABSTRACT

The present invention is an improved means for detecting neuroanatomical pathways in animals comprising introducing an atoxic fragment C of tetanus toxin into the motor target of a neural circuit, and permitting the atoxic fragment to transport through the neural circuitry. The fragment C of tetanus toxin is then localized along the neuroanatomical pathway by reacting the fragment C with monospecifically reactive antibody produced by a hybridoma cell line selected from the group consisting of αTTC-17, αTTC-44, αTTC-49 and αTTC-114. The present invention also includes the individual hybridoma cell lines which produce the reactive antibody along with the antibody themselves.

2 Claims, No Drawings

MEANS FOR DETECTING AND ANALYZING NEUROANATOMY

This is a continuation of application Ser. No. 892,191, filed July 31, 1986, now abandoned.

BACKGROUND OF THE INVENTION

The present invention relates to the art of neuroanatomy, and, in particular, is directed to an improved means for detecting neural circuits. The present invention has resulted in the course of work conducted with funds provided, in part at least, by an award or grant from the National Institute of Health (NIH).

A severe limitation of known neuroanatomical methods known today is that they can only examine the connection between two groups of neurons at one time. Since, however, even simple reflexes result from interactions between three or more neurons, a detailed understanding of the basic neural circuitry is not readily performed by present methods.

Accordingly, efforts have been made to provide a neuroanatomical pathway tracer which will cross more than one neuro junction and which can be readily detected. Recent studies on tetanus toxin have demonstrated that this substance moves retrogradely (i.e, backwards) across synaptic junctions, Schwab and Thoenen, "Selective Transsynaptic Tetanus Toxin After Retrograde Axonal Transport in Peripheral Symphetic Nerves," *BRAIN RESEARCH* 122: 459–474 (1977). Thus, this tracer can reveal not just connected pairs of neurons, but also connections between three or more neurons in a single experiment. For example, when tetanus toxin is introduced to neuron A, the tracer moves backwards to neuron B which terminates on neuron A. Then the tracer continues backwards through the nervous system to label the neuron C which, in turn, synapses on neuron B, thereby identifying the neural circuit C-B-A. This feature provides a tremendous tool in determining neuro anatomical circuitry. There are, however, two serious problems regarding the use of tetanus toxin in the nervous system. Tetanus toxin is highly toxic, and the toxin can only be crudely localized by conjugation to $I^{125}$, which is highly radioactive.

Thus, it is an object of the present invention to provide an effective neural pathway tracer which can be readily localized for analysis, while at the same time, providing a safe tracer agent which can be used without adverse side effects to the host.

SUMMARY OF THE INVENTION

The present invention is an improved means for determining a neuroanatomical pathway by providing a safe, effective tracing method which includes introducing the atoxic fragment C of tetanus toxin to the motor target of a neural circuit, e.g., a muscle, permitting the atoxic fragment to transport through the neural circuit, and localizing the neuroanatomical pathway by reacting the fragment C with a monospecifically reactive antibody produced from a hybridoma cell line. The hybridoma cell lines which are part of the present invention include αTTC-17, αTTC-44, αTTC-49, and αTTC-114.

As a result of the present invention a highly specific and intense immuno reactive staining has been provided for those nerve cells and fibers that contain transported fragment C. Consequently, the several time consuming experiments required in the old pathway tracing methods have been eliminated and it is now possible to define precisely the several links in a nerve circuit of the brain in only one experiment.

DETAILED DESCRIPTION OF THE INVENTION

Present investigators have been faced with the difficulties of using a highly effective tracer, such as tetanus toxin, which has undesirable toxic side effects usually associated with the use of the toxin. Thus, they have cast about for an alternative neuroanatomical tracing agent which would provide the same neuro pathway transport without the undesirable side effects. In the attempt to provide nontoxic tracing agent to overcome these problems a nontoxic "C" fragment of tetanus toxin was decided upon. Studies in that direction demonstrated that the neurons transported the "C" fragment retrogradely across two or more synapses, but it was also important to provide an efficient method for localizing the neuroanatomical pathway in order to be able to analyze the pathway. One known method would be to use the immunohistochemical reaction of a serum antibody to the fragment C of tetanus toxin. Accordingly, a serum antibody was used in experiments only to discover that it did not bind well to the C fragment of the tetanus toxin.

Faced with the problem of providing a sufficiently reactive localizing agent, the inventors gave consideration to the work of Kohler and Milstein who reported the establishment of continuous hybrid cell line (hybridoma) derived by the fusion of murine myeloma cells to spleen cells from an immunized mouse which secreted monoclonal antibody to sheep red blood cells: *Nature:* Volume 256, 495 (1975). Thus, it has been proposed to prepare an antibody monospecifically reactive with the fragment C of tetanus toxin, preferably produced by a monoclonal producing hybridoma, if possible, so that consistent localization of the C fragment can be made.

Thus, six week old female Balb/c mice were inoculated interperitoneally, at one week intervals for four consecutive weeks, with 25 μg/inoculam tetanus toxin fragment C (TTC) in the presence of complete (first inoculation) or incomplete (subsequent inoculations) Freund's adjuvant. Fourteen days following the last inoculation, each mouse was boosted with 10–20 μg TTC inoculation (without adjuvant). Four days later, the mice were sacrificed, the spleens removed, and subjected to fusion procedure in accordance with Kohler and Milstein, 1975 and Lipsich, Lewis and Brugge, protocol, 1983, with the non-secretor mouse myeloma line P3X63Ag8.653 (obtained from the Salk Institute, San Diego, Calif.) using polyethylene-glycol-1300-1600 (ATTC). The cells were distributed to 96 well plates and successfully fused hybridomas were selected by growing the cells in RPMI-1640 (Grand Island Biological), 10% NCTC 1090 (Grand Island Biological) with 20% fetal calf serum (Hyclone Labs) containing 0.1 mM hypoxanthine, 0.4 mM aminopterine and 0.01 mM thymidine and rat thymus conditioned media.

Medium samples were taken from wells containing clones, two weeks after the fusion and assayed for antibody using Enzyme-linked Immunosorbent Assay (ELISA). A total of 408 clones were tested with about 115 giving a positive response. After the growing of the clones to a larger volume (1-3 ml) media samples were retested using ELISA. 29 positives were grown and frozen stocks were made.

However, a final screening was done on media from 12 of the 29 clones resulting in 4 excellent positives. This was done by immunohistochemical staining of sections of pigeon ciliary ganglion after injection of tetanus toxin fragment C into the anterior chamber of the eye. The criterion for selection was strength of immunoreactive staining in cells and presynaptic endings of the ganglion.

It has been found that the strain αTTC-44 provided a very positive response with both assay methods, and has been subcloned using limited dilution to ensure monoclonality and for further use in accordance with the present invention. Furthermore, the hybrid cell lines αTTC-49, αTTC-17 and αTTC-114 were also found to consistently produce a very reactive antibody to atoxic fragment C of tetanus toxin.

Experiments have since been conducted to demonstrate the efficacy of use of nontoxic fragment C of tetanus toxin as a neuro pathway tracing tool in combination with the monoclonal antibodies described herein which can be used to localize the nontoxic fragment C of the tetanus toxin to provide detection of the neuro transport of the fragment C through the neuroanatomical circuitry. In particular, a comparison of the retrograde transsynaptic transport of fragment C of tetanus toxin with direct retrograde transport of horseradish peroxidase (HRP) in a vestibuloocular pathway was conducted to show that a localization of fragment C with a monoclonal antibody provides direct retrograde transsynaptic labelling method for determining pathways in the central nervous system.

Light microscopic examination of brainstem sections, following injection of fragment C of tetanus toxin to the superior oblique muscle of the pigeon revealed direct retrograde transport of the fragment C into the contralateral trochlear nucleus and clear transsynaptic transport into the vestibular nuclei.

Direct retrograde labeling with HRP showed the location and distribution of motoneurons innervating the superior oblique muscle. Twenty-four hours after placing the IVth nerve of two birds in a cuff containing 40% HRP (in Tris buffer, pH 7.4), the birds were perfused with an avian saline solution followed by administration of a fixative of 1% paraformaldehyde and 1.25% glutaraldehyde in phosphate buffer (pH 7 4). Fifty micron sections of the brain were cut on a freezing microtome, reacted with the tetramethyl benzidine method modified for glucose oxidase and counterstained with neutral red. Reconstruction of the trochlear nucleus demonstrated that all neurons innervated the contralateral superior oblique muscle and that no labelling occurred in the ipsilateral nucleus.

Then an injection of fragment C of tetanus toxin into the superior oblique muscle labelled the same population of motoneurons as that backfilled by an HRP injection. Eight days after injection of 20 μl of a 5% solution of fragment C (Calbiochem) into three pigeons, the birds were perfused with 6% dextran in PB followed by a fixative of 4% paraformaldehyde in PB. Thirty-five micron section of the brain were cut on a freezing microtome, incubated with a monoclonal antibody raised 1:500), followed by incubation with biotinylated antimouse IgG. The tissue was treated using standard protocol for the Avidin-Biotin procedure (Vector Labs) reacted with diaminobenzidine (DAB). The absence of labelling in the ipsilateral trochlear nucleus or in the neurons other than those known to terminate on trochlear motoneurons confirmed that nonspecific binding did not occur.

All contralateral trochlear motoneurons, but no motoneurons contained reaction product following a fragment C injection, but no motoneurons ipsilateral to the injected superior oblique muscle contained the reacted antibody The pattern of staining differs from that associated with HRP. First, fragment C appears to bind to the membrane rather than filling the inside of the cell. Indeed, the staining gives the impression that the synaptic boutons surrounding the motoneurons contain label. Second, the staining associated with fragment C extends well outside the nucleus into the medial longitudinal fasiculus (MLF) and surrounding reticular formation. To confirm that this is dendritic staining, experimentation determined the soma-dendritic organization of trochlear motoneurons with intracellular staining using HRP.

Four trochlear motoneurons in three pigeons were penetrated with micropipettes containing 10% HRP (in equal amounts of Tris buffer pH 7.4 and 0.5 M KCl), antidromically identified by stimulation of the IVth nerve, and tested for vestibular responses by electrical stimulation of the VIIIth nerve. All motoneurons exhibited, at disynaptic latencies, an epsp from stimulation of the contralateral VIIIth nerve and an ipsp from stimulation of the ipsilateral VIIIth nerve. HRP was then ionophoresed into the neurons with steps of positive current ranging from 10 to 20 nA with a 75% duty cycle. One hour after the injection, the bird was perfused with avian saline solution followed by the fixative used in the HRP protocol. One hundred micron sections of the brain were cut on a freezing microtome and reacted with diaminobenzidine, and counterstained with cresyl violet. Reconstruction of each motoneuron revealed the same broad dendritic field extending into the MLF and stretching laterally into the surrounding reticular formation. Thus, the extent of the dendritic arbor of intracellularly stained motoneurons corresponds to the pattern of labelling resulting from direct retrograde transport of fragment C to motoneurons. This implies that in addition to reaching the soma, fragment C also spreads throughout the dendritic tree of the trochlear motoneurons.

The populations of vestibular neurons labeled transsynaptically by injections of fragment C into the superior oblique muscle are nearly the same as the vestibular neurons backfilled directly by a large HRP injection into the trochlear nucleus. Fragment C, however, labels more cells in each nucleus than does the HRP. In order to identify which vestibular nucleus neurons project into the trochlear nucleus, HRP was pressure-injected into the trochlear nucleus of two pigeons. Twenty-four hours later the birds were perfused with avian saline solution and fixative. The brains were treated as described for the extracellular HRP experiments. In both cases, the HRP injection filled the trochlear nucleus, as well as extending rostrally into the inferior rectur subdivision of the oculomotor nucleus, and spreading dorsally into the reticular formation. The illustrated injection retrogradely labelled neurons bilaterally in the nucleus tangentalis, the lateral vestibular nucleus, neurons contralaterally in the descending vestibular nucleus, the medial vestibular nucleus and neurons in the ipsilateral superior vestibular nucleus which extend into the immediately rostral dorsal lateral vestibular nucleus. The fragment C muscle injection transsynaptically labels similar populations of vestibular neurons as does the HRP injection into the trochlear nucleus, except for the rostrally located ipsilateral superior vestibular and lateral vestibular nuclei. Fragment C, however, surpasses the HRP injection in the number of labelled neurons in each cf the nuclei. The absence of fragment C-labelled neurons in the ipsilateral superior vestibular nucleus may suggest that fragment C does not move transsynaptically across these synapses. Alternatively, the large HRP injection may have labelled afferents terminating outside the trochlear nucleus or fibers of passage.

Accordingly, immunohistochemical localization of transsynaptically transported fragment C offers important advantages over the HRP techniques for identifying disynaptic pathways. First, it has been demonstrated that the transport of the fragment C to premotor afferent neurons shows that fragment C labels a larger number of neurons than does direct retrograde HRP. While the present invention is not to be in any way unlimited by theories as to the reason for this enhanced staining, it probably results from retrograde transport of fragment C to not only the soma of the motoneuron, but also to its distal dendrites, potentially exposing all afferent synapses to the tetanus toxin fragment. An HRP injection confined to the cytoarchitectonic boundaries of a nucleus (as defined by soma distribution) would miss afferent input on dendrites extending outside of the nucleus. Second, discrete HRP injections into nuclei containing motoneurons innervating more than one muscle (e.g., oculomotor nucleus, facial nucleus) are virtually impossible. Injection of fragment C directly into a muscle with subsequent transsynaptic transport obviates this problem. Third, HRP injections invariably label fibers passing through the injection site. Fourth, unlike the transsynpatic transport of WGA-HRP, which must be facilitated by electrical stimulation of afferent axons, transsynaptic labelling with fragment C requires no special treatment. Consequently, when localized with a monoclonal antibody, tetanus toxic fragment C is a reliable and powerful transsynaptic retrograde marker for neuroanatomical research.

Thus, while there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

We claim:

1. A process for tracing a neuroanatomical pathway in non-human animals comprising:
    inserting or injecting atoxic fragment C of tetanus toxin in an amount sufficient to react with an antibody into a neuroanatomical pathway of an active neural circuit of said animal,
    permitting said atoxic fragment to transport directly and/or transsynaptically through the neural circuit,
    removing a section containing said neuroanatomical pathway from the animal,
    preparing the section for immunoreaction with antibody,
    immunohistochemically localizing said transported fragment C within the neural circuit with a monoclonal antibody produced by a hybridoma cell line said monoclonal antibody being specific for transported fragment C,
    said localizing comprised of allowing said transported fragment C and said monoclonal antibody to form in vitro a detectable immunohistochemical reaction product at areas in the neural circuit to which fragment C has been transported so that the neuroanatomical pathway is thereby traced.

2. The process of claim 1 which further comprises staining the immunohistochemical reaction product.

* * * * *